United States Patent [19]

Porta et al.

[11] 4,097,528

[45] Jun. 27, 1978

[54] [N-(2-DIPHENYLMETHOXYETHYL)-N-(1-METHYL-2-PHENOXYETHYL)-N-METHYL] AMINE

[75] Inventors: Angel Lázaro Porta; Antonio Ibáñez Paniello, both of Barcelona, Spain

[73] Assignee: Doctor Andreu, S.A., Spain

[21] Appl. No.: 819,900

[22] Filed: Jul. 28, 1977

[30] Foreign Application Priority Data

Aug. 5, 1976 Spain ................................. 450.500
Aug. 5, 1976 Spain ................................. 450.501
Aug. 5, 1976 Spain ................................. 450.502
Aug. 5, 1976 Spain ................................. 450.503

[51] Int. Cl.$^2$ ............................................ C07C 93/08

[52] U.S. Cl. ............................ 260/570 R; 260/501.18; 260/611 A; 260/612 D

[58] Field of Search ..................... 260/501.18, 570 R

[56] References Cited

U.S. PATENT DOCUMENTS

| | | | |
|---|---|---|---|
| 3,565,955 | 2/1971 | Ehrhart et al. | 260/570 |
| 3,666,811 | 5/1972 | Stett | 260/570 |

*Primary Examiner*—Robert V. Hines
*Attorney, Agent, or Firm*—McGlew and Tuttle

[57] ABSTRACT

A new compound [N-(2-diphenylmethoxyethyl)-N-(1-methyl-2-phenoxyethyl)-N-methyl] amine, its pharmaceutically acceptable salts and its processes of preparation are disclosed. Such salts have a muscle relaxing and vasodilating activity.

1 Claim, No Drawings

[N-(2-DIPHENYLMETHOXYETHYL)-N-(1-METHYL-2-PHENOXYETHYL)-N-METHYL] AMINE

FIELD OF THE INVENTION

The present invention relates to a new compound [N-(2-diphenylmethoxyethyl)-N-(1-methyl-2-phenoxyethyl)-N-methyl] amine having the following structural formula

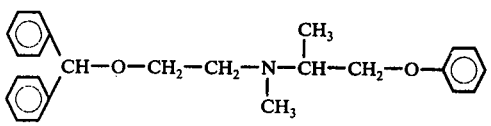 (I)

and to its pharmaceutically acceptable salts having a muscle relaxing and vasodilating activity.

The invention also relates to processes for preparing the above compound.

SUMMARY OF THE INVENTION

One of said processes is characterised in that a diphenyl-methoxy-2-haloethyl ether of the following formula

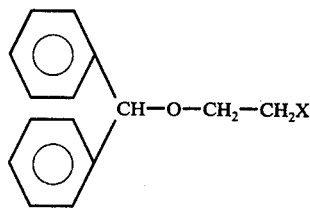 (II)

wherein X is a halogen atom, preferably chlorine, bromine or iodine, is reacted with an amine of the formula

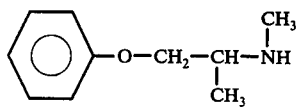 (III)

to provide the compound of formula I. This reaction is conducted in a polar medium such as ethanol, methanol, acetonitrile, dimethylformamide, etc.

A further process is characterised fundamentally by the reaction of a hydroxy-diphenyl methane of the formula

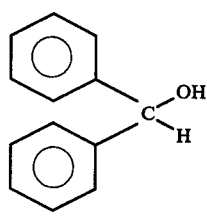 (IV)

with a basic compound of the formula

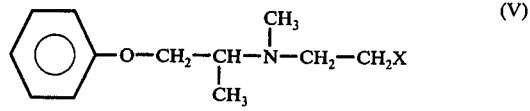 (V)

where X has the same meaning as given above, to obtain the compound of formula I. This reaction is conducted in both high and low polarity solvents and use may also be made of the conventional catalysts for this type of reaction.

A third process is characterised in that the compound: [N-(2-diphenylmethoxyethyl)-N-(1-methyl-2-phenoxyethyl)] amine of the following formula:

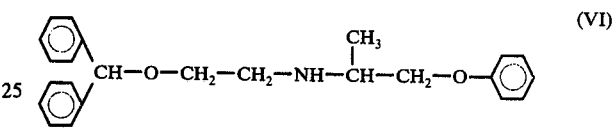 (VI)

is reacted with formaldehyde and thereafter reduced, preferably with formic acid or metal hydrides.

Finally, a further process is characterised by the reaction of [N-2-(diphenylmethoxyethyl)-N-methyl] amine having the formula:

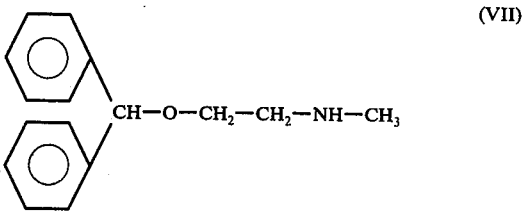 (VII)

with a halo-1-methylphenoxyethane of the formula:

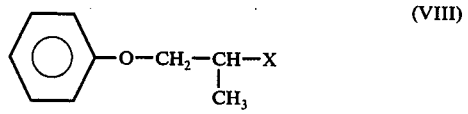 (VIII)

where X has the same meaning as given above. This reaction is conducted in methanol, ethanol, benzene, toluene, acetonitrile, dimethylformamide or any other appropriate medium.

The salt of the compound of formula I may be prepared with a conventional acid such as citric, tartaric, succinic, fumaric, α-ketoglutaric, lactic, etc. acid to form crystalline compounds having medicinal applications.

The new compound as described, in the form of an acid salt with citric acid, having the formula

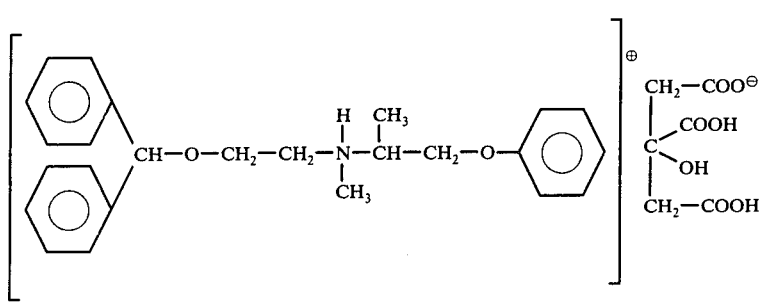

was subjected to pharmacological tests and its toxicity values in the mouse were:
$LD_{50}$
oral: 467 mg/Kg
i.p.: 196 mg/Kg
i.v.: 29.3 mg/Kg
and its muscle relaxing activity, being of a musculotrophic type, was subjected to comparative studies with other compounds on intravenous administration. It showed a more potent action than paparverine.

DETAILED DESCRIPTION

EXAMPLE I

Preparation of
[N-(2-diphenylmethoxyethyl)-N-(1-methyl-2-phenoxyethyl)-N-methyl] amine.

A mixture of diphenylmethoxy-2-bromoethylether (18.6 g) and [N-(1-methyl-2-phenoxyethyl)-N-methyl] amine (10.5 g) in absolute ethanol was heated under reflux for 48 hours. The solvent was evaporated at reduced pressure and the resulting residue was poured over a solution of anhydrous sodium carbonate (20 g) in water (300 ml). The resulting emulsion was extracted twice with ether (300 ml), the ether phases were combined, were washed with water several times and dried with anhydrous sodium sulphate. The volatile portions were evaporated at reduced pressure to give 22.3 g of [N-(2-diphenylmethoxyethyl)-N-(1-methyl-2-phenoxyethyl)-N-methyl] amine in the form of a syrupy liquid.

EXAMPLE II

Preparation of
[N-(2-diphenylmethoxyethyl)-N-(1-methyl-2-phenoxyethyl)-N-methyl] amine hemioxalate.

[N-(2-diphenylmethoxyethyl)-N-(1-methyl-2-phenoxyethyl)-N-methyl] amine (97.2 g) was dissolved in absolute ethanol (450 ml) and this solution was added slowly with stirring over a solution of anhydrous oxalic acid (35 g) in absolute ethanol (1000 ml). A crystalline precipitate already started to form during the addition and at the end of the addition the mixture had thickened considerably. The crystalline solid was recovered by filtration and recrystallised in ethanol to give 60 g of [N-(2-diphenylmethoxyethyl)-N-(1methyl-2-phenoxyethyl)-N-methyl] amine (hemioxalate), m.p. 127°–8° C.
IR (KBr):$v$, 3600–3300, 3080–2400, 1710, 1630, 1592, 1491, 1472, 1449, 1395, 1238, 1095, 752, 721, 702, 693 $cm^{-1}$.

EXAMPLE III

Preparation of
[N-(2-diphenylmethoxyethyl)-N-(1-methyl-2-phenoxyethyl)-N-methyl] amine.

Concentrated sulphuric acid (8 ml) was added over a stirred solution of diphenylmethanol (30 g) in benzene (300 ml). Thereafter the mixture was heated under reflux and portions of [N-(2-hydroxyethyl)-N-(1-methyl-2-phenoxyethyl)-N-methyl] amine hydrochloride (35.2 g) were added. After the addition was finished, refluxing and stirring were continued for 4 hours. The mixture was left to cool and water (300 ml) was added with stirring and thereafter anhydrous sodium carbonate until the water phase had an alkaline pH. The water phase was drawn off and the benzene phase was washed twice with water, dried with anhydrous sodium sulphate and the volatile portions were evaporated off at reduced pressure to give 38.4 g of [N-(2-diphenylmethoxyethyl)-N-(1-methyl-2-phenoxyethyl)-N-methyl] amine in the form of a syrupy liquid.

EXAMPLE IV

Preparation of
[N-(2-diphenylmethoxyethyl)-N-(1-methyl-2-phenoxyethyl)-N-methyl] amine.

A mixture of diphenylbromomethane (27.9 g), [N-(2-hydroxyethyl)-N-(1-methyl-2-phenoxyethyl)-N-methyl] amine (23.6 g) and anhydrous sodium carbonate (6.0 g) was heated at 110° C for 3 hours with constant stirring. It was allowed to cool and benzene (200 ml) was added, the solid residue being recovered by filtration at reduced pressure. The filtrate was washed several times with water, dried with anhydrous sodium sulphate and evaporated at reduced pressure to produce 32.6 g of [N-(2-diphenylmethoxyethyl)-N-(1-methyl-2-phenoxyethyl)-N-methyl] amine.

EXAMPLE V

Preparation of
[N-(2-diphenylmethoxyethyl)-N-(1-methyl-2-phenoxyethyl)-N-methyl] amine monocitrate.

[N-(2-diphenylmethoxyethyl)-N-1-methyl-2-phenoxyethyl)-N-methyl] amine (13.2 g) was dissolved in methanol (100 ml) and this solution was added slowly, with stirring over a solution of anhydrous citric acid (7.7 g) in methanol (100 ml). The resulting solution was evaporated to dryness at reduced pressure and the residue formed was treated with anhydrous ethyl ether to form a solid which was recovered by filtration, washed with ethyl ether and thereafter dried under reduced pressure at 50° C to give 18.9 g of [N-(2-diphenylmethoxyethyl)-N-(1-methyl-2-phenoxyethyl)-N-ethyl] amine monocitrate, m.p. 85° C (decomp.).

IR (KBr):ν, 3100–2400, 1725, 1708, 1590, 1492, 1450, 1235, 1172, 1085, 812, 750, 708, 695 cm$^{-1}$.

EXAMPLE VI

Preparation of [N-(2-diphenylmethoxyethyl)-N-(1-methyl-2-phenoxyethyl)-N-methyl] amine.

A mixture of [N-(2-diphenylmethoxyethyl)-N-(1-methyl-2-phenoxyethyl)] amine (9.6 g), anhydrous formic acid (10 ml) and 35% aqueous solution of formaldehyde (6 ml) was heated at 100° C for 3 hours. It was cooled and the reaction liquor was poured over a solution of sodium bicarbonate (5 g) in water (300 ml). It was extracted twice with ethyl ether (300 ml), the ether phases were combined and washed with water several times, dried with anhydrous sodium sulphate and evaporated at reduced pressure to give 8.7 g of [N-(2-diphenylmethoxyethyl)-N-(1-methyl-2-phenoxyethyl)-N-methyl] amine in the form of a syrupy liquid.

EXAMPLE VII

Preparation of [N-(2-diphenylmethoxyethyl)-N-(1-methyl-2-phenoxyethyl)-N-methyl] amine monocitrate.

[N-(2-diphenylmethoxyethyl)-N-(1-methyl-2-phenoxyethyl)-N-methyl] amine (29.3 g) were dissolved in absolute ethanol (100 ml) and this solution was added slowly with stirring over a solution of anhydrous citric acid (17.0 g) in absolute ethanol (200 ml). The resulting solution was cncentrated to a volume of 80 ml and anhydrous ether (150 ml) were added with stirring. The resulting solution was left in a freezer for 24 hours. The result was a crystallised solid which was recovered by filtration at reduced pressure, washed with a mixture of absolute ethanol and absolute ether (1:2) and dried at reduced pressure at 50° C to give 39.2 g of [N-(2-diphenylmethoxyethyl)-N-(1-methyl-2-phenoxyethyl)-N-methyl] amine monocitrate, m.p. 85° C (decomp.).

IR (KBr) : ν, 3100–2400, 1725, 1708, 1590, 1492, 1450, 1235, 1172, 1085, 812, 750, 708, 695 cm$^{-1}$.

EXAMPLE VIII

Preparation of [N-(2-diphenylmethoxyethyl)-N-(1-methyl-2-phenoxyethyl)-N-methyl] amine.

A mixture of [N-(2-diphenylmethoxy) ethyl-N-methyl] amine (31.6 g) 1-chloro-1-methyl-2-phenoxyethane (21.5 g) potassium iodide (0.3 g), pyridine (5 ml) and acetonitrile (350 ml) was heated under reflux for 2 hours. The volatile portions were evaporated off under reduced pressure and the resulting residue was treated with a solution of anhydrous sodium carbonate (30 g) in water (500 ml). It was extracted with ether twice and the ether phases were combined, washed wth water several times, dried with anhydrous sodium sulphate and the solvent was evaporated off under reduced pressure to give 29.3 g of [N-(2-diphenylmethoxyethyl)-N-(1-methyl-2-phenoxyethyl)-N-methyl] amine in the form of a viscous liquid.

EXAMPLE IX

Preparation of [N-(2-diphenylmethoxyethyl)-N-(1-methyl-2-phenoxyethyl)-N-methyl] amine hemioxalate.

A solution of anhydrous oxalic acid (16.2 g) in methanol (150 ml) was added over a solution of [N-(2-diphenylmethoxyethyl)-N-(1-methyl-2-phenoxyethyl)-N-methyl] amine (44.9 g) in methanol (150 ml). The resulting solution was concentrated to a volume of about 50 ml and ether (200 ml) was added to cause the precipitation of a solid which was recovered by filtration under reduced pressure. The solid was washed with a small amount of ethyl ether and dried under reduced pressure at 50° C to give 50 g of [N-(2-diphenylmethoxyethyl)-N-(1-methyl-2-phenoxyethyl)-N-methyl] amine hemioxalate, m.p. 127°–8° C.

IR (KBr) : ν, 3600–3300, 3080–2400, 1710, 1630, 1592, 1491, 1472, 1449, 1395, 1238, 1095, 752, 721, 702, 693 cm$^{-1}$.

What we claim is:

1. [N-(2-diphenylmethoxyethyl)-N-(1-methyl-2-phenoxyethyl)-N-methyl] amine of the following structural formula:

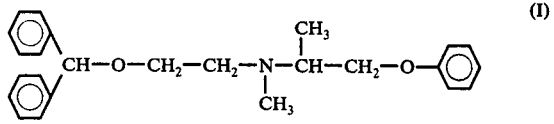

(I)

and its pharmaceutically acceptable salts.

* * * * *